United States Patent
Peters

(10) Patent No.: US 9,445,979 B2
(45) Date of Patent: Sep. 20, 2016

(54) HAIR TREATMENT COMPOSITION CONTAINING GAMBOGIC ACID, ESTER OR AMIDE

(75) Inventor: Eva Peters, Berlin (DE)

(73) Assignee: DSM IP ASSETS B.V., Heerlen (NL)

(*) Notice: Subject to any disclaimer, the term of this patent is extended or adjusted under 35 U.S.C. 154(b) by 364 days.

(21) Appl. No.: 13/640,636

(22) PCT Filed: Apr. 12, 2011

(86) PCT No.: PCT/EP2011/055724
§ 371 (c)(1),
(2), (4) Date: Mar. 18, 2013

(87) PCT Pub. No.: WO2011/128339
PCT Pub. Date: Oct. 20, 2011

(65) Prior Publication Data
US 2013/0195777 A1    Aug. 1, 2013

(30) Foreign Application Priority Data
Apr. 12, 2010  (EP) .................................... 10159608

(51) Int. Cl.
| | |
|---|---|
| *A61K 8/49* | (2006.01) |
| *A61Q 5/00* | (2006.01) |
| *A61Q 5/06* | (2006.01) |
| *A61Q 7/00* | (2006.01) |
| *A61K 8/97* | (2006.01) |
| *A61Q 5/10* | (2006.01) |
| *A61Q 5/12* | (2006.01) |
| *A61Q 5/02* | (2006.01) |

(52) U.S. Cl.
CPC ............... *A61K 8/498* (2013.01); *A61K 8/97* (2013.01); *A61Q 5/00* (2013.01); *A61Q 5/06* (2013.01); *A61Q 5/10* (2013.01); *A61Q 5/12* (2013.01); *A61Q 7/00* (2013.01); *A61Q 5/002* (2013.01); *A61Q 5/02* (2013.01)

(58) Field of Classification Search
CPC .......... A61K 8/498; A61K 8/97; A61Q 5/10; A61Q 5/002; A61Q 5/02; A61Q 5/12; A61Q 7/00
See application file for complete search history.

(56) References Cited

U.S. PATENT DOCUMENTS

2005/0261363 A1*  11/2005  Lee et al. .............. 514/453
2006/0051311 A1    3/2006  Walter et al.
2007/0093456 A1*   4/2007  Cai et al. .............. 514/151

FOREIGN PATENT DOCUMENTS

| FR | 2 716 374 |   | 8/1995 |
| FR | 2716374 | * | 8/1995 |
| JP | 9-143036 |   | 6/1997 |
| WO | WO 2008/148008 |   | 12/2008 |

OTHER PUBLICATIONS

Nishimura et al, Mechanisms of Hair garying: Incomplete melanocyte stem cell maintenance in the niche, Science vol. 307, pp. 720-723, 2005.*
International Search Report for PCT/EP2011/055724, mailed Jul. 1, 2011.
Written Opinion of the International Searching Authority for PCT/EP2011/055724, mailed Jul. 1, 2011.
Panthong et al., "Anti-inflammatory, analgesic and antipyretic activities of the extract of gamboge from Garcinia hanburyi Hook f", Journal of Ethnopharmacology, vol. 111, No. 2, (Apr. 5, 2007), pp. 335-340.
Asano, et al., "Cytotoxic xanthonones from garcinia hanburyi", Phytochemistry, vol. 41, No. 3, (Jan. 1, 1996), pp. 815-820.
Database WPI, Week 200733, AN 2007-349381 & JP 2007-106674, (Apr. 26, 2007), 8 pages.

* cited by examiner

*Primary Examiner* — Mina Haghighatian
(74) *Attorney, Agent, or Firm* — Nixon & Vanderhye P.C.

(57) ABSTRACT

The present invention relates to a cosmetic composition comprising compounds or salts of formula (I) or formula (II), wherein R1 and R2 are both independently hydrogen (H), or a saturated, straight or branched $C_1$-$C_8$ alkyl group. More particularly, the present invention also relates to the use of said cosmetic composition for the prevention of the graying of hair and/or for restoration and/or maintenance of the natural hair color.

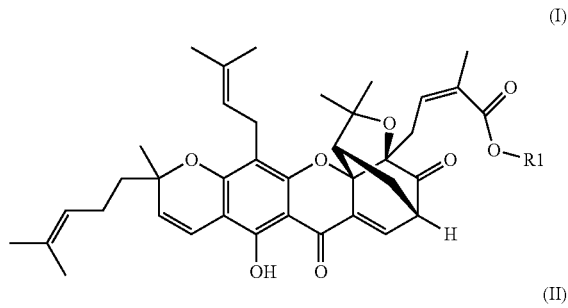

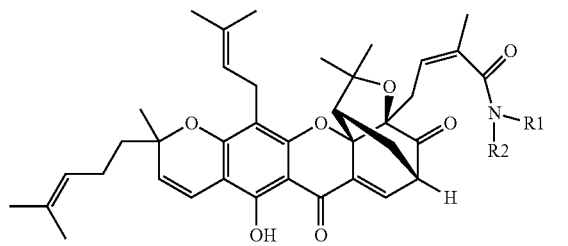

5 Claims, No Drawings

HAIR TREATMENT COMPOSITION CONTAINING GAMBOGIC ACID, ESTER OR AMIDE

This application is the U.S. national phase of International Application No. PCT/EP2011/055724, filed 12 Apr. 2011, which designated the U.S. and claims priority to EP Application No. 10159608.8, filed 12 Apr. 2010, the entire contents of each of which are hereby incorporated by reference.

The present invention relates to a cosmetic composition comprising gambogic acid, or a salt, an ester, or an amide thereof as depicted in formula (I) or formula (II). More particularly, the present invention relates to the use of said cosmetic composition for the prevention of the graying of hair and/or for restoration and/or maintenance of the natural hair color, to restore or enhance hair growth.

Furthermore, the invention relates to a method for preventing the graying of hair and/or restoring and/or maintaining the natural hair color which comprises the step of applying to skin having hair of a human a topical composition comprising an effective amount of gambogic acid, or a salt, an ester, or an amide thereof as depicted in formula (I) or formula (II).

The present invention also relates to the use of gambogic acid, or a salt, an ester, or an amide thereof as depicted in formula (I) or formula (II) for increasing the total number of melanocytes in hair follicles and/or for increasing the differentiation and migration of melanocytes from the hair sheath to the hair matrix.

Hair graying is an obvious sign of aging in human, yet its mechanism until now remains largely unknown. The hair is composed of a protein called keratin. The hair itself is arranged in three layers, an outer cuticle, middle cortex and central medulla. If the hair is colored, it is due to the presence of pigments—either melanin (black or brown) or pheomelanin (red or yellow). If these pigments are lacking, the hair is white. Canities is the term given to grey hair, it is an illusion created by the mixture of white and colored hairs. Hair grows from a follicle. The walls of the follicle form the outer root sheath of the hair. The lower part of the follicle widens out to form the hair bulb that contains the germinal matrix, the source of hair growth. Dermal tissue projects into the follicle base to form the dermal papilla, and this has a network of capillary blood vessels to supply oxygen, energy, and the amino-acids needed for growth.

Melanocytes are present in the hair bulb above the upper part of the dermal papilla, producing pigment granules (melanosomes) that are transferred to the hair shaft forming epithelial cells (keratinocytes) and distributed throughout the cortex. Together, they form the pigmentary unit of the hair follicle. In the follicle, an inner root sheath that has three layers surrounds the hair. The Henle's layer is one cell thick and is in the middle of the sheath. Huxley's layer is two or three cells thick and is in the middle of the sheath. The cuticle of this inner root sheath interlocks with the cuticle of the hair. Both the hair and the inner root sheath grow at the same rate, but the inner root sheath breaks down about two-thirds of the way up the follicle, so only the hair emerges past the skin surface.

It is well known in the art that hair turn white due to gradual disappearance of melanocytes from the hair follicle (Tobin 2009, Int. J. Trichology 1(2): 83-93). This process affects both the melanocytes of the pigmentary unit located at the base of the hair follicle and directly responsible for the pigmentation of the hair fiber, as well as progenitor melanocytes located in the distal portion of the outer sheath of the hair follicle which act as a reservoir from which the pigmentation unit is renewed on each hair cycle (Van Neste and Tobin 2004, Micron 35:193-200).

Correcting the effects of aging as far as possible is a preoccupation of ever-increasing importance. In this context, white hair which is deemed to be unsightly is very often caused to disappear using coloring treatment shampoos. Clearly, however, although that technique has proved effective in nullifying the effects of hair graying, it has no effects on its causes. Therefore, that solution is temporary, and needs to be frequently renewed as the hair grows.

It therefore remains a long awaited need in the hair care industry to prevent age related graying of the hair, to prevent loss of natural coloration of the hair, and even to promote restoration of the natural hair color not only because of its lasting effects but because of its visual documentation of the capacity to halt the aging process.

The inventors of the present application now surprisingly found that gambogic acid derivatives as described below have a great potential as cosmetic compositions, and for use in hair care applications for prevention of the graying of hair and/or for restoration and/or maintenance of the natural hair color, as shown by the ability of said compounds and derivatives to increase total number of melanocytes in hair follicles, as well as, to increase the differentiation and migration of melanocytes from the hair sheath to the hair matrix.

Therefore, in a first embodiment, the present invention provides a cosmetic composition comprising a compound of formula (I) or formula (II), or a salt of said compounds,

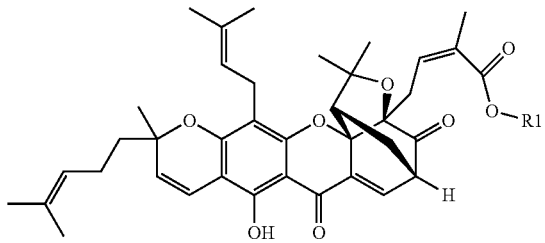

Formula (I)

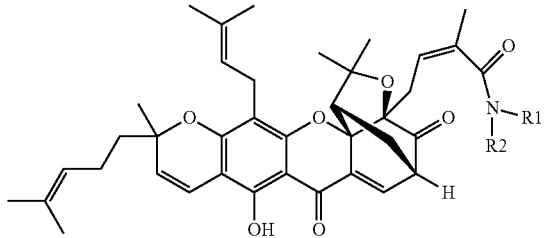

Formula (II)

wherein R1 and R2 are both independently hydrogen (H), or a saturated, straight or branched $C_1$-$C_8$ alkyl group.

It is to be understood that both formula (I) and formula (II) as depicted above encompass all possible stereoisomers.

In the above definition of compounds of formula (I) or formula (II), preferred R1 and R2 groups are both independently hydrogen, methyl, ethyl, propyl, isopropyl, butyl, sec. butyl, isobutyl, pentyl, neopentyl, hexyl, 2-ethyl-hexyl, heptyl, and octyl. It is well understood that any lower alkyl group containing three or more carbon atoms can be either straight chain or branched chain.

Most preferred R1 and/or R2 alkyl groups are chosen from methyl, ethyl, and propyl.

The salts of gambogic acid or amide derivative of formula (I) or formula (II) may be formed by any cosmetically acceptable cation which means any metal cation as well as any organic cation that is not toxic to the skin and/or does not cause allergic reactions. Examples of such cations are ammonium salts and alkyl ammonium salts, alkali cations such as sodium and potassium ions and alkaline earth metal cations such as calcium and magnesium ions.

In a particular embodiment, the R1 group is hydrogen, thereby defining the compound of formula (I) as gambogic acid or a salt of said acid, and compounds of formula (II) as primary or secondary amide derivatives of gambogic acid, wherein R2 is hydrogen, methyl, ethyl, propyl, isopropyl, butyl, sec. butyl, isobutyl, pentyl, neopentyl, hexyl, 2-ethylhexyl, heptyl, or octyl. Any lower alkyl group containing three or more carbon atoms can be either straight chain or branched chain. The most preferred R2 alkyl group thereof is chosen from methyl, ethyl, and propyl.

In a preferred embodiment, the cosmetic composition comprises gambogic acid, gambogic amide, or a salt of said compounds encompassing all possible stereoisomers.

The most preferred composition according to the present invention comprises gambogic amide according to the formula (II), wherein both R1 and R2 are hydrogen, and with the stereochemistry as depicted in formula (III) with the following CA index name: 2-Butenamide, 2-methyl-4-[(1R,3aS,5S,11R,14aS)-3a,4,5,7-tetrahydro-8-hydroxy-3,3,11-trimethyl-13-(3-methyl-2-buten-1-yl)-11-(4-methyl-3-penten-1-yl)-7,15-dioxo-1,5-methano-1H,3H,11H-furo[3,4-g]pyrano[3,2-b]xanthen-1-yl]-, (2Z)- and the following CAS number (286935-60-2)

Formula (III)

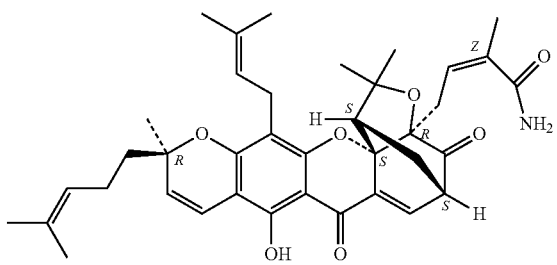

In another embodiment, cosmetic compositions according to the following invention comprise the crude gamboge resin comprising gambogic acid and/or gambogic amide, or a natural extract from the resin exuded from the *Garcinia handburryi* tree as described in WO2008/148008.

The compounds of the present invention can be sourced from chemical suppliers like e.g.: Sigma. Gambogic acid can easily be purified by preparation of a pyrimidine salt of a crude extract from gamboge resin followed by repeated re-crystallization of the salt in ethanol. This resin is exuded from *Garcinia handburyi* tree, a tree growing in Asia. Purification methods have been described in WO2008/148008. Furthermore, gambogic amide can be prepared from gambogic acid as a precursor using standard amidation chemical reactions and also as described in P.N.A.S. (2007), 104: 16329-16334.

In another embodiment, the cosmetic composition according to the present invention may further comprise auxiliary agents (carriers and/or excipients or diluents) conventionally used in cosmetic compositions, and more particularly in topical hair care compositions.

Suitable auxiliary agents conventionally used in hair care compositions according to the present invention are chosen from those disclosed in general terms in Ullmann's Encyclopedia of Industrial Chemistry (1989), Vol. A 12, Hair Preparations, and more specifically, e.g., in International Patent Application No. WO 00/06094, WO 00/07550 and WO 01/06994.

In yet another embodiment, the cosmetic composition according to the present invention comprises a compound of formula (I), formula (II), or formula (III) as described above, in an amount comprised between 0.00001 wt.-% and 20 wt.-% by weight of the total composition. Preferred amount according to the present invention is comprised between 0.0001 wt.-% and 1 wt.-% by weight of the total composition.

Preferred cosmetic compositions according to the present invention are topical hair care compositions in the form of cosmetic hair-treatment preparations, e.g. hair tonics, conditioners, hair-care preparations, e.g. pre-treatment preparations, styling creams, styling gels, pomades, hair rinses, treatment packs, intensive hair treatments e.g. leave-on and rinse-off deep conditioners, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile.

Most preferred hair care compositions are leave-on compositions selected from hair tonics, conditioners, treatments, and styling gels.

Based on the application the hair care preparations may be in the form of a (aerosol) spray, (aerosol) foam, gel, gel spray, cream, lotion, liquid or a wax. Hair sprays comprise as well aerosol sprays as pump sprays without propellant. Hair foams comprise as well aerosol foams as pump foams without propellant. Hair sprays and hair foams comprise mainly or exclusively water soluble or water dispersible components. If the components used in hair sprays or hair foams according to the invention are water dispersible, then they may be in the form of micro dispersions with particle sizes of usually 1 to 350 nm, preferably 1 to 250 nm. The solid content of such preparations is typically in the range of 0.5 to 20 wt.-% of the total weight of the preparation. Such micro dispersions normally do not need further emulsifiers or tensides for their stabilization.

Thus, compositions according to the present invention may contain further ingredients to protect the hair against detrimental environmental impact and to improve the health of the hair. Therefore, hair care compositions according to the present invention may comprise additional cosmetic or dermatological adjuvants and/or additives (cosmetic carrier) which are preferably selected from 1.) Water
2.) Water soluble organic solvents, preferably C1-C4-Alkanols
3.) Oils, fatty substances, waxes
4.) Various esters different to 3) of C6 to C30 monocarboxylic acids with mono-, di-, or trivalent alcohols
5.) Saturated acyclic and cyclic hydrocarbons
6.) Fatty acids
7.) Fatty alcohols
8.) Silicone oils
9.) Surface active ingredients
and mixtures thereof.

The hair care compositions can contain further adjuvants and additives such as preservatives, antioxidants, silicones, thickeners, softeners, anionic, cationic, non-ionic or amphoteric emulsifiers, light screening agents, antifoaming agents, moisturizers, fragrances, surfactants, fillers, sequestering agents, anionic, cationic, non-ionic or amphoteric polymers or mixtures thereof, propellants, acidifying or basifying agents, dyes, colorants, pigments or nanopigments, light stabilizers, insect repellents, antibacterial agents, or any other ingredients usually formulated into hair care compositions. The necessary amounts of the adjuvants and additives can, based on the desired product, easily be chosen by a skilled artisan in this field and will be illustrated in the examples, without being limited hereto.

An exemplary hair gel with the compound of the present invention may comprise:
1. 0.1 to 20 wt.-% preferably 1 to 10 wt.-% of at least one hair polymer;
2. 0 to 10 wt.-% of at least one carrier (solvent), selected from C2-C5 alcohols, preferably ethanol;
3. 0.01 to 5 wt.-%, preferably 0.2 to 3 wt.-% of at least one thickener;
4. 0 to 50 wt.-% of a propellant;
5. 0 to 10 wt.-%, preferably 0.1 to 3 wt.-% of a styling polymer different to 1.), preferably a water soluble non-ionic polymer;
6. 0 to 1 wt.-% of at least one refatter, preferably selected from glycerine and glycerine derivatives;
7. 0 to 30 wt.-% of other customary additives e.g. a silicone component
8. 0.005 to 5 wt.-% of a compound of formula (I) or formula (II) according to the present invention,
9. water ad 100 wt.-%

An exemplary conditioner preparation according to the present invention may comprise:
1. 0.05 to 10 wt.-% of a hair polymer
2. 5 to 95 wt.-% of water
3. 5 to 50 wt.-% of surfactant
4. 0 to 5 wt.-% of an additional conditioning agent
5. 0 to 10 wt.-% other customary additives
6. up to 20 wt.-% of a compound of formula (I) or formula (II) according to the present invention,
all ingredients adding up to 100 wt.-%.

An exemplary styling composition with the compound of the present invention may comprise:
1. 0.1 to 10 wt.-% of at least one hair polymer;
2. 20 to 99 wt.-% water and/or alcohol;
3. 0 to 70 wt.-% of at least one propellant;
4. 0 to 20 wt.-% of customary additives;
5. 0.005 to 5 wt.-% of a compound of formula (I) or formula (II) according to the present invention.

An exemplary styling gel with the compound of the present invention may comprise:
1. 0.1 to 10 wt.-% of a hair polymer;
2. 60 to 99.85 wt.-% of water and/or alcohol;
3. 0.05 to 10 wt.-% of a gel former;
4. 0 to 20 wt.-% of other customary additives.
5. 0.005 to 5 wt.-% of a compound of formula (I) or formula (II) according to the present invention.

An exemplary hair care composition (spray) with the compound of the present invention may comprise:
1. 0.005 to 5 wt.-% of a compound of formula (I) or formula (II) according to the present invention,
2. 30 to 99.5 wt.-%, preferably 40 to 99 wt.-%, of at least one solvent chosen from water, water-miscible solvents and mixtures thereof;
3. 0 to 70 wt.-% of propellant;
4. 0.1 to 10 wt.-% of at least one water-soluble or water-dispersible hair polymer
5. 0 to 0.3% by weight of at least one water-insoluble silicone;
6. 0 to 0.5 wt.-% of at least one wax, preferably at least one fatty acid amide;
7. customary additives.

Another hair care composition with the compound of the present invention may comprise:
1. 0.05 to 20 wt.-% of at least one hair polymer;
2. 20 to 99.95 wt % of water and/or alcohol;
3. 0 to 79.5 wt.-% of customary additives;
4. 0.005 to 5 wt.-% of a compound of formula (I) or formula (II) according to the present invention.

An exemplary composition for aerosol foams with the compound of the present invention may comprise:
1. 0.1 to 10 wt.-% of at least one hair polymer;
2. 55 to 99.8 wt.-% water and/or alcohol;
3. 5 to 20 wt.-% of a propellant;
4. 0.1 to 5 wt.-% of an emulsifier;
5. 0 to 10 wt.-% of customary additives.
6. 0.005 to 5 wt.-% of a compound of formula (I), or formula (II) according to the present invention.

The hair care composition according to the invention can comprise at least a water-soluble or water-dispersible hair polymer. Typical hair polymers for use in the present invention are commercially available polymers for hair care such as hair styling or conditioning polymers such as e.g. copolymers of vinyl acetate and crotonic acid, copolymers of methyl vinyl ether and maleic anhydride, copolymers of acrylic acid or methacrylic acid with other monomers, polyurethanes, N-vinylpyrrolidone and silicone polymers.

The content of the hair polymer is generally from about 0.1 to 10% by weight, based on the total weight of the composition. Here, it is preferable to use water-soluble or water-dispersible polyurethanes which, if desired, additionally comprise siloxane groups in copolymerized form.

The composition according to the invention can further comprise, at least one water-insoluble silicone, in particular a polydimethylsiloxane, e.g. the Abil® grades from Goldschmidt. The content of the silicone is then generally from about 0.0001 to about 2% by weight, preferably from about 0.001 to about 1% by weight, based on the total weight of the composition. Preferred waxes according to the present invention are fatty acid amides, such as, for example, erucamide.

The hair care compositions according to the present invention can, where appropriate, additionally comprise an antifoaming agent, e.g. based on silicone. The amount of anti-foaming agent is generally up to 0.001% by weight, based on the total amount of the composition. The compositions according to the invention have the advantage that, on the one hand, they impart the desired hold to the hair and, on the other hand, the polymers are easy to wash out (redispersible). Generally, a natural appearance and shine is imparted to the hair, even when the hair is by its very nature especially thick and/or dark.

The term alcohol refers to all alcohols usually used in cosmetic compositions such as ethanol, n-propanol, isopropanol.

Other suitable ingredients according to the present invention are cosmetic adjuvants and additives such as propellants, anti-foaming agents, surface active ingredients e.g. tensides, emulsifiers, foam former and solubilisators. The used surface active ingredients may be anionic, cationic, amphoteric or neutral. Further ingredients may be preservatives, antioxidants, perfume oils, lipidic refatters, active and/or caring ingredients such as panthenol, collagen, vitamins, protein hydrolysates, alpha- and beta hydroxyl carbonic acids, stabilisators, pH regulators, opacifiers, colorants, dyes, gel formers, salts, moisturizers, complex formers, viscosity regulators or light screening agents without being limited thereto.

In order to obtain certain properties the hair care compositions may additionally comprise conditioning compounds based on silicone such as polyalkylsiloxane, polyarylsiloxane, polyarylalkylsiloxane, silicone resins, polyethersiloxane or dimethicone copolyole (CTFA) and amino functionalized silicone compounds such as amodimethicone (CTFA), GP 4 Silicone Fluid® and GP 7100® (Genesee), Q2 8220® (Dow Corning), AFL 40® (Union Carbide) or polymers as disclosed in EP-B 852 488.

Other suitable ingredients comprise silicone propfpolymers having a polymeric silicone backbone and non-silicone containing side chains or a non silicone containing polymeric backbone and silicone side chains such as Luviflex® Silk or polymers disclosed in EP-B 852 488.

Typical propellants for hair sprays or aerosol foams may be used. Preferred are mixtures of propane/butane, pentane, dimethylether, 1,1-difluoroethane (HFC-152a), carbon dioxide, nitrogen or compressed air.

All emulsifiers for aerosol foams, or surfactants for shampoo preparations may be conventionally used non-ionic, cationic, anionic or amphoteric emulsifiers/surfactants.

Examples of non-ionic emulsifiers are (INCl-nomenclature) Laureths, (e.g. Laureth-4); Ceteths, (e.g. Ceteth-1, polyethyleneglycolcetylether); ceteareths, e.g. ceteareth-25, polyglycol fatty acid glycerides, hydroxylated lecithins, lactyl esters of fatty acids, alkylpolyglycosides.

Examples of non-ionic surfactants are e.g. reaction products of aliphatic alcohols or alkylphenols with 6 to 20 C-Atoms of a linear or branched alkyl chain with ethyleneoxide and/or propyleneoxide. The amount of alkyleneoxide is about 6 to 60 mol to one mol alcohol. Furthermore alkylaminoxide, mono- or dialkylalkanolamide, fatty esters of polyethylene glycols, alkylpolyglycosides or sorbitan ester are suitable for the incorporation of hair care compositions according to the invention.

Examples of cationic emulsifiers/surfactants are quaternised ammonium compounds e.g. cetyltrimethylammonium chloride or bromide (INCl: cetrimonium chloride or bromide), stearyl benzyl dimethylammonium chloride, distearyldimethylammonium chloride, stearamidopropyldimethylamine, hydroxyethylcetyldimonium phosphate (INCl: Quaternium-44), Luviquat® Mono LS (INCl: Cocotrimoniummethosulfate), poly(oxy-1,2-ethandiyl), (octadecylnitrilio)tri-2,1-Ethandiyl)tris-(hydroxy)-phosphate (INCl Quaternium-52). Furthermore, cationic guar derivatives such as guarhydroxypropyltrimonium chloride (INCl) may be used in conditioner/shampoo preparations.

Anionic emulsifiers/surfactants can be selected from alkylsulfate, alkylethersulfate, alkylsulfonate, alkylarylsulfonate, alkylsuccinate, alkylsulfosuccinate, N-alkylsarkosinate, acyltaurate, acylisethionate, alkylphosphate, alkyletherphosphate, alkylethercarboxylate, alpha-olefinsulfonate, especially the alkali-und earth alkali salts, e.g. sodium, potassium, magnesium, calcium, as well as ammonium- and triethanol amine-salts. The alkylethersulfate, alkyletherphosphate and alkylethercarboxylate may comprise between 1 to 10 ethyleneoxide or propyleneoxide units, preferably 1 to 3 ethyleneoxide-units per molecule.

Suitable anionic surfactants are e.g. sodium laurysulfate, ammonium laury sulfate, sodium laurylethersulfate, ammonium laurylethersulfate, sodium lauroylsarkonisate, sodiumoleylsuccinate, ammonium laurylsulfosuccinate, sodium dodecylbenzolsulfonate, triethanolamidodecylbenzolsulfonate.

Suitable amphoteric surfactants are e.g. alkylbetaine, alkylamidopropylbetaine, alkylsulfobetaine, alkylglycinate, alkylcarboxyglycinate, alkylamphoacetate or propionate, alkylamphodiacetate or dipropionate such as cocodimethylsulfopropylbetaine, laurylbetaine, cocamidopropylbetaine or sodium cocamphopropionate.

As gel formers, all typical cosmetic gel formers can be used such as slightly cross linked polyacrylic acid e.g. Carbomer (INCl), cellulose derivatives, polysaccharides e.g. xanthan gum, caprylic/capric triglyceride (INCl), sodiumacrylate-copolymers, polyquaternium-32 (and) paraffinum liquidum (INCl), sodiumacrylate-copolymers (and) paraffinum liquidum (INCl) (and) PPG-1 trideceth-6, polyquaternium-37 (and) propyleneglycoldicapratdicarylate (and) PPG-1 trideceth-6, polyquaternium-7, polyquaternium-44.

In order to provide the formulation a pearlescent appearance or to give the impression of a richer or creamier product, the hair care composition may additionally comprise opacifiers and/or pearly gloss-imparting substances, such as soaps or salts of carboxylic acids, cationics including cationic polymers, dimethicone (INCl) or amodimethicone (INCl).

Customary additives are for example long chain fatty alcohols such as cetyl alcohol, stearyl alcohol, cetylstearyl alcohol, dimethylstearamine. Furthermore the hair care composition may contain lipids such as dimethicone, amodimethicone, mineral oil, or silicon derivatives such as Dimethicone Copolyol.

The present invention also provides the use of a composition as described above for the prevention of the graying of hair, for restoration and/or maintenance of the natural hair color, and/or to enhance and/or restore hair growth.

More preferably, the present invention provides the use of a composition as described above for the prevention of the graying of hair, for restoration and/or maintenance of the natural hair color, and/or to enhance and/or restore hair growth.

The compounds of formula (I) or formula (II) such as in particular gambogic amide of formula (III) may be used to prevent hair graying as well as to restore and/or maintain the natural hair color in mammals.

The efficacy of the use of compounds of formula (I) or formula (II) in accordance with the present invention for prevention of the graying of hair and/or for restoration and/or maintenance of the natural hair color can be shown as exemplified in the examples, or by procedures described below:

As a reference (control) a hair tress containing approximately 100 hairs is cut neatly above the scalp. The color of the hair within the tress is measured from the near-root part to the tip. This could be either done 1) visually by scoring, 2) with high density photo documentation and scoring, 3) by pigment analysis and determination of the melanin content from hair following hair degradation and melanin extraction. In this later case, melanin can be measured by photometric means, or by chemical reaction (i.e.: formation of pyrrole-2,3,5 tricarboxylic acid from eumelanin, and formation of aminohydroxyphenylalanine isomers for pheomelanin, followed by quantitative chromatographic, spectroscopic, or spectrophotometric analysis.

A sample of the topical composition (2-10 mL or mg/cm$^2$, depending on the type of formulation; preferably a leave-on product such as hair tonic, lotion or cream) containing preferred amount of a compound of formula (I) or formula (II) is then applied at least once a day on the scalp, typically from 1 to 4 times daily for at least three months, especially six months (because normal hair grow rate is about 1 cm/month) and distributed equally with a massage on the scalp. The product should not be washed out after application. At the end of the treatment period, a second hair sample is taken from the same place on the scalp and analyzed as described above.

A comparison of the melanin content, hair color or degree of graying is made intra-individually before and after the treatment period.

In another embodiment, the invention further provides the use of the cosmetic composition according to the present invention, wherein the composition as defined above further comprises at least one additional active substance selected from the group consisting of antioxidants, light screening agents, colorants and biological actives as described below.

Thus, the use of compounds of formula (I) or formula (II) according to the present invention may be combined with the use of further ingredients to protect the hair against detrimental environmental impact and to improve the health of the hair.

Antioxidants

Based on the invention all known antioxidants usually formulated into hair care compositions can be used. Especially preferred are antioxidants chosen from the group consisting of amino acids (e.g. glycine, histidine, tyrosine, tryptophan) and their derivatives, imidazole (e.g. urocanic acid) and derivatives, peptides such as D,L-carnosine, D-carnosine, L-carnosine and derivatives (e.g. anserine), carotenoids, carotenes (e.g. α-carotene, β-carotene, lycopene) and derivatives, chlorogenic acid and derivatives, lipoic acid and derivatives (e.g. dihydrolipoic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-; oleyl-, y-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteinesulfoximine, buthioninsulfone, penta-, hexa-, heptathioninsulfoximine) in very low compatible doses (e.g. pmol to µmol/kg), additionally (metal)chelators (such as α-hydroxyfatty acids (citric acid, lactic acid, malic acid), palmic-, phytinic acid, lactoferrin), β-hydroxyacids, huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate and ascorbyltetraisopalmitate, Mg-ascorbylphosphate, Na-ascorbylphosphate, ascorbyl-acetate), tocopherol and derivates (such as vitamin-Eacetate), mixtures of nat. vitamin E, vitamin A and derivatives (vitamin-A-palmitate and acetate) as well as coniferylbenzoate, rutinic acid and derivatives, α-glycosylrutin, ferulic acid, furfurylideneglucitol, carnosine, butylhydroxytoluene, butylhydroxyanisole, trihydroxybutyrophenone, urea and its derivatives, mannose and derivatives, zinc and derivatives (e.g. ZnO, $ZnSO_4$), selen and derivatives (e.g. selenomethionin), stilbenes and derivatives (such as stilbenoxide, trans-stilbenoxide) and suitable derivatives (salts, esters, ethers, sugars, nucleotides, nucleosides, peptides and lipids) of the named active ingredients, or enzymes such as superoxide dismutase, catalase or similar, or activators of such enzymes. One or more preservatives/antioxidants may be present in an amount of at least 0.01 wt.-% of the total weight of the composition. Preferably about 0.01 wt.-% to about 10 wt.-% of the total weight of the composition of the present invention is present. Most preferred, one or more preservatives/antioxidants are present in an amount about 0.1 wt.-% to about 1 wt.-%.

Light Screening Agents

Light screening agents are advantageously selected from UV-A, UV-B and/or broadband filters. Examples of UV-B or broad spectrum screening agents, i.e. substances having absorption maximums between about 290 and 340 nm may be organic or inorganic compounds. Organic UV-B or broadband screening agents are e.g. acrylates such as 2-ethylhexyl 2-cyano-3,3-diphenylacrylate (octocrylene, PARSOL® 340), ethyl 2-cyano-3,3-diphenylacrylate and the like; camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like; Cinnamate derivatives such as ethylhexyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes; p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate; benzophenones such as benzophenone-3, benzophenone-4,2,2',4,4'-tetrahydroxy-benzophenone, 2,2'-dihydroxy-4,4'-dimethoxybenzophenone and the like; esters of benzalmalonic acid such as di-(2-ethylhexyl) 4-methoxybenzalmalonate; esters of 2-(4-ethoxy-anilinomethylene) propandioic acid such as 2-(4-ethoxy anilinomethylene) propandioic acid diethyl ester as described in the European Patent Publication EP 0895 776; organosiloxane compounds containing benzmalonate groups as described in the European Patent Publications EP 0358584 B1, EP 0538431 B1 and EP 0709080 A1 such as polysilicone-15 (PARSOL® SLX); drometrizole trisiloxane (Mexoryl XL); imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of prim., sec. and tert. amines like monoethanol amine salts, diethanol amine salts and the like; salicylate derivatives such as isopropylbenzyl salicylate, benzyl salicylate, butyl salicylate, ethylhexyl salicylate (PARSOL® EHS, NEO Heliopan OS), isooctyl salicylate or homomethyl salicylate (homosalate, PARSOL® HMS, NEO Heliopan OS) and the like; triazine derivatives such as ethylhexyl triazone (Uvinul T-150), diethylhexyl butamido triazone (Uvasorb HEB). Encapsulated UV-filters such as encapsulated ethylhexyl methoxycinnamate (Eusolex UVpearls) or microcapsules loaded with UV-filters as e.g. disclosed in EP 1471995 and the like. Inorganic compounds are pigments such as microparticulated $TiO_2$, ZnO and the like. The term "microparticulated" refers to a particle size from about 5 nm to about 200 nm, particularly from about 15 nm to about 100 nm. The $TiO_2$ particles may also be coated by metal oxides such as e.g. aluminum or zirconium oxides or by organic coatings such as e.g. polyols, methicone, aluminum stearate, alkyl silane. Such coatings are well known in the art.

Examples of broad spectrum or UV A screening agents i.e.: substances having absorption maximums between about 320 and 400 nm may be organic or inorganic compounds e.g.: dibenzoylmethane derivatives such as 4-tert. butyl-4'- methoxydibenzoyl-methane (PARSOL® 1789), dimethoxydibenzoylmethane, isopropyldibenzoylmethane and the like; benzotriazole derivatives such as 2,2'-methylene-bis-(6-(2H-benzotriazole-2-yl)-4-(1,1,3,3,-tetramethylbutyl)-phenol (TINOSORB M) and the like; bis-ethylhexyloxyphenol methoxyphenyl triazine (Tinosorb S) and the like; phenylene-1,4-bis-benzimidazolsulfonic acids or salts such as 2,2-(1,4-phenylene)bis-(1H-benzimidazol-4,6-disulfonic acid) (Neoheliopan AP); amino substituted hydroxybenzophenones such as 2-(4-diethylamino-2-hydroxybenzoyl)-benzoic acid hexylester (Uvinul A plus) as described in EP 1046391; Ionic UV-A filters as described in WO 2005/080341 A1; pigments such as microparticulated ZnO or $TiO_2$ and the like. The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g. 3,3-Diphenylacrylate derivatives as described in EP 0 514 491 B1 and EP 0 780 119 A1; Benzylidene camphor derivatives as described in the U.S. Pat. No. 5,605,680; Organosiloxanes containing benzmalonate groups as described in the EP 0 358 584 B1, EP 0 538 431 B1 and EP 0 709 080 A1.

Colorants

Based on the invention, all colorants usually formulated into hair care compositions which have an absorption in the visible light of electromagnetic radiation (400-800 nm) can be used. The absorption is often caused by the following chromophores: Azo- (mono-, di-, tris-, or poly-)stilbene-, carotenoide-, diarylmethane-, triarylmethane-, xanthene-, acridine-, quinoline-, methine- (also polymethine-) thiazol-, indamine-, indophenol-, azin-, oxazine-, thiazine-, anthraquinone-, indigo-, phthalocyanin and further synthetic, natural and/or inorganic chromophores.

FD&C (United States Federal Food Drug and Cosmetic act) and D&C which can be used in hair care compositions according to the invention are e.g. curcumin, riboflavin, lactoflavin, tartrazine, quinoline yellow, cochenille, azorubin, amaranth, ponceau 4R, erythrosine, red 2G, indigotin, chlorophyll, chlorophyllin, caramel, carbo medicinalis, carotenoids, carotin, bixin, norbixin, annatto, orlean, capsanthin, capsorubin, lycopin, xanthophyll, flavoxanthin, lutein, kryptoaxanthin, rubixanthin, violaxanthin, rhodoxanthin, canthaxanthin, betanin, anthocyans without being limited thereto. Examples of dyes are e.g. inorganic pigments such as iron oxide (iron oxide red, iron oxide yellow, iron oxide black etc.) ultramarines, chromium oxide green or carbon black. Other colorants and dyes which can be used in the compositions according to the invention comprise natural or synthetic organic pigments, disperse dyes which may be solubilized in solvents like direct hair dyes of the HC type, for example HC red No. 3, HC Blue No. 2 and all other hair dyes listed in International Cosmetic Ingredient Dictionary Handbook, 11th edition, 2006) or the dispersion dyes listed in Color Index International Society of Dyers and Colorist, color varnishes (insoluble salts of soluble dyes, like many Ca-, Ba- or Al-salts of anionic dyes), soluble anionic or cationic dyes such as acid dyes (anionic), basic dyes (cationic), direct dyes, reactive dyes or solvent dyes, fluorescent dyes, fluorescein and isothiocyanates.

Biological Actives.

Biological actives are advantageously selected from general activators of melanogenesis like tyrosinase activators, peptide hormones, cAMP-activators and neurotrophins.

Preferred tyrosinase activators are any substance which increases tyrosinase expression or enzyme activity, like e.g. glycyrrhizin from the root of licorice.

Peptide hormones belonging to the group of melanocortins are the preferred peptide hormones including ACTH, alpha-MSH, beta-MSH and gamma-MSH; these peptides are all cleavage products of a large precursor peptide called pro-opiomelanocortin (POMC). Alpha-MSH is the most important melanocortin for pigmentation. The melanocyte-stimulating hormones (collectively referred to as MSH or intermedins) are a class of peptide hormones that in nature are produced by cells in the intermediate lobe of the pituitary gland. They stimulate the production and release of melanin (melanogenesis) by melanocytes in skin and hair. Therefore, they will be advantageously combined with the compounds of the present invention.

The invention further provides a method for preventing the graying of hair and/or restoring and/or maintaining of the natural hair color, and/or to enhance and/or restore hair growth, said method comprising the step of applying to skin having hair of a human a topical composition comprising an effective amount of a compound of formula (I) or formula (II).

The term skin having hair relates to all parts of the skin having hair such as in particular the scalp and the face (eyelashes, the eyebrows, beard). Most preferably the topical compositions are applied to the scalp of humans (male or female of any age).

The effective amount to be used in the method according to the invention refers to an amount necessary to obtain a physiological effect. The physiological effect may be achieved by one single dose or by repeated doses. The dosage administered may, of course, vary depending upon known factors, such as the physiological characteristics of the particular composition and its mode and route of administration; the age, health and weight of the recipient; the nature and extent of the symptoms; the kind of concurrent treatment; the frequency of treatment; and/or the effect desired and can be adjusted by a person skilled in the art.

The term "effective amount" means generally at least 0.00001 wt.-% based on the total weight of the topical composition. Preferably, the topical compositions contain the compound of formula (I) or formula (II) according to the present invention in an amount of 0.00001 wt.-% to 20 wt.-%, most preferably in an amount from 0.0001 wt.-% to 1 wt.-% based on the total weight of the composition.

Preferably, the topical compositions are applied at least twice a day such as e.g. once in the morning and once in the evening.

The term "topical composition" as used herein denotes to any composition suitable for the topical application to mammalian keratinous tissue such as skin having hair, particularly to the human scalp. In particular the topical compositions are hair care compositions such as conditioners, treatments, tonics, styling gels, mousses, shampoos, hair sprays, pomades, setting lotions, coloring and permanent waving compositions. Of particular interest for the purpose of the present invention are tonics, conditioners, treatments, and styling gels which may be in the form of a gel, a lotion, a tincture, a spray, a mousse, a cleansing composition or a foam and which may be applied according to individual needs, e.g., once daily as a lotion, tincture, mousse or spray; or once or twice weekly as a conditioner or treatment.

The typical composition used in the method for preventing the graying of hair as well as for restoring and/or maintaining the natural hair color according to the present invention may further comprise other ingredients which are conventionally used in topical compositions such as 5,6-dihydroxyindoline HBr, 5,6-dihydroxyindoline HBr in combination with 2-methylresorcinol and/or arginine.

The present invention further provides the use of compounds of formula (I) or formula (II) as described in this invention for increasing the total number of melanocytes in the hair follicle and/or for increasing the differentiation and migration of melanocytes from the hair sheath to the hair matrix.

Number of melanocytes in the hair follicle can be evaluated by standard methods e.g.: immunohistochemical staining of the melanocytes with the pan-melanocyte marker NKI-beteb following by counting the NKI-beteb+ cells.

Differentiation and migration of melanocytes from the hair sheath to the hair matrix can be measured by immunohistochemical staining of c-kit+ melanocytes in the hair follicle, and by assessing their distribution within the hair follicle.

The invention is illustrated further by the Examples which follow without being limited thereto.

Macroscopic analysis of hair follicle pigmentation showed a slow loss of active pigmentation in the control group over the 7 day culture period (in vitro graying). A clear and significant improvement of hair follicle pigmentation was observed at concentration comprised between 0.1 to 1 micro molar GA which was effectively able to maintain hair follicle pigmentation in the cultured anagen hair follicle.

Immunohistochemical analysis of hair follicle was performed according to standard methods. Immunohistochemical staining of the pan-melanocyte marker NKI-beteb and the proliferation marker Ki67 was used to asses total number of melanocytes in cultured follicles in presence of GA. When GA was used in concentrations between 0.1 and 0.5 micro molar, the total number of melanocytes was increased in hair follicles that remained in the anagen stage of the hair cycle. This increase was dose dependent. This observation indicates an enhanced maintenance of a pigmentary unit by GA and mobilization of the melanocyte reservoir in the outer root sheath.

Using Trp2 as a marker for melanocyte precursors we found a higher number of Trp2+ melanocytes in control hair follicles. These cells were mainly found in the pigmentary-unit indicating a residual melanocyte-precursor population in this compartment. These results were confirmed by the results obtained with labeling of cKit, a marker for migrating, activated early melanocytes which was most pronouncedly found in hair follicles treated between 0.1 and 1 micro molar GA.

The results are summarized in Table 1 below:

| GA | Hair shaft elongation | Hair cycle progression | Pigmentation | Dystrophy | Melanocyte dendricity | Total number melanocytes | Ki67 | Trp2 | cKit |
|---|---|---|---|---|---|---|---|---|---|
| control | + | − | + | − | ++ | ++ | − | ++ | (+) |
| 10 nMol | +(+) | − | − | − | ++ | ++(+) | − | − | ++ |
| 50 nMol | ++ | − | − | − | +++ | ++ | − | (+) | ++(+) |
| 100 nMol | +(+) | − | +(+) | − | +++ | +++ | (+) | − | +++ |
| 500 nMol | +++ | − | +(+) | − | +++ | +++ | + | + | ++ |
| 1000 nMol | +++ | (+) | ++ | − | +++ | + | − | − | +++ |

EXAMPLES

Example 1

Effect of Gambogic Amide on Cultured Hair Follicles

Tissue containing human hair follicles in the growth stage (anagen) of the hair cycle were obtained from elective facial surgery interventions. Hair follicles were isolated and maintained in culture according to methods well established in the art (Philpott et al. 1990, J Cell Sci. 97: 463-471). Gambogic amide (GA) was administered to pigmented cultured anagen VI hair follicle every other day over a culture period of 7 days in various concentrations comprised between 10 nano molar and 1 micro molar and compared to a control group without addition of GA.

Hair shaft elongation was measured as a way to assess possible hair growth promoting or inhibiting effects of GA. At concentrations comprised between 0.1 and 1 micro molar, an increase in hair shaft elongation was measured when compared to control even if no hair cycle progression was observed with the application of GA. No signs of toxicity were observed at concentrations as high as 1 micro. It is therefore concluded from this first observation that the dose range in which GA can be used is between 10 nano molar and 1 micro molar, and that GA can be used as a hair growth promoting or restoring agent.

Example 2

Anti Dandruff Shampoo

| INCI NOMENCLATURE | wt.-% |
|---|---|
| Aqua | Ad 100 |
| Ammonium Laureth Sulphate | 35.00 |
| Ammonium Lauryl Sulphate | 15.00 |
| Glycol Distearate | 1.00 |
| Dimethicone | 1.00 |
| Cetyl Alcohol | 0.50 |
| Cocamide MEA | 3.00 |
| ZPT | 1.00 |
| Guar Hydroxipropyltrimonium Chloride | 0.20 |
| Hydrogenated Polydecene | 1.00 |
| Polyquaternium-10 | 0.10 |
| PEG 7m | 0.50 |
| Trimethylpropane Tricaprylate/Tricaprate | 1.00 |
| Preservative | q.s. |
| Parfum | 0.30 |
| E 104, E 110, E 132 | 0.02 |
| Compound of formula (I) or formula (II) according to the present invention such as in particular gambogic amide | 0.01 |

Combine all ingredients and mix intensively until a homogeneous solution is obtained. At the end add the water under slow agitation and wait until the foam has disappeared.

Example 3

Conditioner Shampoo

| INCI NOMENCLATURE | wt.-% |
| --- | --- |
| Aqua | Ad 100 |
| Sodium Laureth Sulphate | 25.00 |
| Cocamidopropyl Betaine | 5.00 |
| Sodium Chloride | 2.50 |
| Glycol Distearate | 1.00 |
| Glycerin | 2.00 |
| Dimethiconol | 0.50 |
| Parfum | 0.50 |
| Coco-Glucoside | 3.00 |
| Carbomer | 0.10 |
| Arginine | 0.05 |
| Glyceryl Oleate | 0.05 |
| Glyceryl Stearate | 1.00 |
| Guar Hydroxypropyltrimonium Chloride | 0.10 |
| Panthenol | 1.00 |
| Disodium EDTA | 0.05 |
| Preservative | q.s. |
| Hydrolyzed Keratin | 0.10 |
| Citric Acid/Sodium Hydroxide | q.s |
| Compound of formula (I) or formula (II) according to the present invention such as in particular gambogic amide | 0.005 |
| E 102, E 110, FD&C blue | 0.01 |

Combine all ingredients and mix intensively until a homogeneous solution is obtained. At the end add the water under slow agitation and wait until the foam has disappeared. Then add carefully the thickening agent like sodium chloride.

Example 4

Shampoo with Plant Extracts

| INCI NOMENCLATURE | wt.-% |
| --- | --- |
| Aqua | Ad 100 |
| Sodium Laureth Sulfate | 25.00 |
| Lauryl Glucoside | 10.00 |
| Cocamidopropyl Betaine, | 5.00 |
| Propylene Glycol | 2.0 |
| Perfume | 1.25 |
| Sodium Citrate | 0.25 |
| Sodium Benzoate | 0.20 |
| Panthenol | 1.00 |
| Sodium Formate | 0.20 |
| Polyquaternium-10 | 0.20 |
| Hydroxypropyl Guar Hydroxypropyltrimonium Chloride | 0.05 |
| PEG-35 Castor Oil | 1.00 |
| Maris Sal | 1.25 |
| Polysorbate 20 | 1.00 |
| Tocopheryl Acetate | 0.20 |
| Prunus Armeniaca (Apricot) Fruit Extract | 0.20 |
| Echinacea Purpurea Extract | 0.05 |
| Retinyl Palmitate | 0.05 |
| Tocopherol | 0.05 |
| Linoleic Acid | 0.20 |
| Preservative | 1.00 |
| Compound of formula (I) or formula (II) according to the present invention such as in particular gambogic amide | 0.01 |
| CI 77891 | 0.02 |

Combine all ingredients and mix intensively until a homogeneous solution is obtained. At the end add the water under slow agitation and wait until the foam has disappeared.

Example 5

Shine Shampoo

| INCI NOMENCLATURE | wt.-% |
| --- | --- |
| Aqua | Ad 100 |
| Sodium Laureth Sulfate | 15.00 |
| Disodium Cocoamphodiacetate | 15.00 |
| Sodium Chloride | 2.00 |
| Glycol Distearate | 1.00 |
| Cocamidopropyl PYL Betaine | 2.00 |
| Laurdimonium Hydroxypropyl Hydrolyzed Wheat Protein, | 1.00 |
| PEG-12 Dimethicone | 1.00 |
| Guar Hydroxypropyltrimonium Chloride | 0.05 |
| Hydrolyzed Wheat Protein | 0.20 |
| Laureth-4 | 1.00 |
| PEG-7 Glyceryl Cocoate | 2.00 |
| Hydrogenated Castor Oil | 1.00 |
| Laureth-2 | 0.50 |
| PEG-55 Propylene Glycol Oleate, | 2.00 |
| Propylene Glycol | 2.00 |
| Mica | 0.20 |
| Citric Acid | 0.01 |
| Parfum | 1.00 |
| E 110, E 104, E 122 | 0.05 |
| Compound of formula (I) or formula (II) according to the present invention such as in particular gambogic amide | 0.05 |

Combine all ingredients and mix intensively until a homogeneous solution is obtained. At the end add the water under slow agitation and wait until the foam has disappeared. Than add carefully the thickening agent like sodium chloride.

Example 6

Hydrating Shampoo for Color Protection

| | INCI Nomenclature | wt.-% |
| --- | --- | --- |
| 1 | Sodium Laureth Sulfate | 45.00 |
| | Polysilicone-15 | 0.30 |
| | Methylchloroisothiazolinone & Methylisothiazolinone | 0.10 |
| | Panthenol | 1.00 |
| | PEG-7 Glyceryl Cocoate | 2.00 |
| | Cocamidopropyl Betaine | 10.00 |
| | Glycol Distearate (and) Glycerin (and) Laureth-4 & Cocamidopropyl Betaine | 2.00 |
| | Disodium EDTA | 0.10 |
| | Parfum | 0.80 |
| | Polyquaternium-10 | 0.10 |
| | Decyl Glucoside | 10.00 |
| 2 | Aqua | Ad 100 |
| | Compound of formula (I) or formula (II) according to the present invention such as in particular gambogic amide | 0.01 |
| | Sodium Chloride | 1.50 |
| | PEG-18 Glyceryl Oleate/Cocoate | 1.00 |

Add all ingredients of part 1 and mix intensively until a homogeneous solution is obtained. Add the water under slow agitation and wait until the foam has disappeared. Than add carefully the thickening agent like Sodium Chloride or Crothix LVR.

Example 7

Extra Shine Revitalizing Hair Cream

| | INCI Nomenclature | wt.-% |
|---|---|---|
| 1 | *Simmondsia Chinensis* (Jojoba) Seed Oil | 3.00 |
| | *Prunus Armeniaca* (Apricot) Kernel Oil | 3.00 |
| | Phenyl Trimethicone | 2.00 |
| | C12-15 Alkyl Benzoate | 2.00 |
| | Glyceryl Stearate SE | 2.00 |
| | Polysilicone-15 | 0.50 |
| | Tocopheryl Acetate | 0.50 |
| | Cetearyl Alcohol | 1.60 |
| 2 | Aqua | Ad 100 |
| | Compound of formula (I) or formula (II) according to the present invention such as in particular gambogic amide | 0.005 |
| 3 | Behentrimonium Chloride | 1.00 |
| | Cocodimonium Hydroxypropyl Hydrolyzed Wheat Protein | 0.30 |
| | Propylene Glycol (and) Diazolidinyl Urea (and) Methylparaben (and) Propylparaben | 1.00 |

Heat part 1 and part 2 separately to 65° C. under moderate agitation. When both have the same temperature add part 2 into part 1 under agitation. Let cool to 40° C. and add part 3 under agitation, homogenize. Cool to ambient temperature.

Example 8

Hair Repair Treatment

| | INCI NOMENCLATURE | wt.-% |
|---|---|---|
| A | Cetearyl Octanoate | 0.20 |
| | Phytantriol | 0.10 |
| | PEG-40 Hydrogenated Castor Oil | 2.00 |
| B | Parfum | q.s. |
| | Cocotrimonium Methosulfate | 2.00 |
| C | Aqua | Ad 100 |
| D | Polyquaternium-16 | 2.00 |
| | Dimethicone Copolyol | 1.00 |
| | Compound of formula (I) or formula (II) according to the present invention such as in particular gambogic amide | 0.5 |
| | Parfum | q.s. |
| | Alcohol denat. | 10.00 |
| | Citric Acid | q.s. |

Heat Part A to 70° C. Add part B to part A under stirring. Add the mixture to part C and homogenize. Add part D and let cool down under moderate agitation.

Example 9

Color Balm

| | INCI NOMENCLATURE | wt.-% |
|---|---|---|
| A | Ceteareth-6, Stearyl Alcohol | 1.50 |
| | Ceteareth-25 | 1.50 |
| | Cetearyl Alcohol | 3.00 |
| | Cetearyl Octanoate | 6.00 |
| | Phytantriol | 0.30 |
| B | Polyquaternium-44 | 7.70 |
| | Compound of formula (I) or formula (II) according to the present invention such as in particular gambogic amide | 0.005 |
| | Propylene Glycol | 2.00 |
| | Panthenol | 1.00 |
| | Parfum | q.s. |
| | Aqua | Ad 100 |
| C | C.I. 42510, Basic Violet 14 | 0.05 |
| | C.I. 12245, Basic Red 76 | 0.08 |
| | Preservative | q.s. |
| | Citric Acid | q.s. |

Heat parts A and B separately to 70° C. Add part A to B and homogenize. Add part C under stirring.

Example 10

Silky Hair Cocktail

| | INCI NOMENCLATURE | wt.-% |
|---|---|---|
| A | Caprylic/Capric Triglyceride (and) Acrylates Copolymer | 3.00 |
| | Dimethicone Copolyol | 0.50 |
| | Dimethicone Copolyol | 2.00 |
| | Cyclomethicone (and) Dimethiconol | 3.00 |
| | Amodimethicone (and) Cetrimonium Chloride (and) Trideceth-10 | 2.00 |
| | Phenyl Trimethicone | 2.00 |
| | Macadamia (Ternifloria) Nut Oil | 1.00 |
| | Tocopheryl Acetate | 0.50 |
| | PEG-40 Hydrogenated Castor Oil | 1.00 |
| | Parfum | q.s. |
| B | Aqua | Ad 100 |
| | Aminomethyl Propanol | 0.46 |
| | Compound of formula (I) or formula (II) according to the present invention such as in particular gambogic amide | 0.01 |
| | PEG/PPG-25/25 | 4.00 |
| | Dimethicone/Acrylates Copolymer | |
| | Preservative | q.s. |

Heat parts A and B separately to 70° C. Add part A to B and homogenize. Let cool down under stirring.

Example 11

Oil Sheen Moisturizer

| | INCI NOMENCLATURE | wt.-% |
|---|---|---|
| A | Cetyl Alcohol | 2.00 |
| | PEG-75 Lanolin | 1.00 |
| | Glyceryl Stearate | 4.00 |
| | Ceteareth-25 | 1.00 |
| | Cetearyl Octanoate | 4 |
| B | Glycerin | 10.00 |
| | Compound of formula (I) or formula (II) according to the present invention such as in particular gambogic amide | 0.05 |
| | Propylene Glycol | 2.00 |
| | Cocotrimonium Methosulfate | 1.00 |
| | Trimethylsilylamodimethicone, SM 2115 Octoxynol-40, Isolaureth-6, Glycerin | 1.50 |
| | Polysorbate 20 | 1.00 |
| | Aqua | Ad 100 |
| C | Panthenol | 0.50 |
| | Preservative | q.s. |
| | Parfum | q.s. |
| | Citric Acid | q.s. |

Heat parts A and B separately to 70° C. Add part A to B and homogenize. Add part C under stirring.

Example 12

Setting Cream High Gloss

| | INCI NOMENCLATURE | wt.-% |
|---|---|---|
| A | Cetyl Alcohol | 5.00 |
| | Glyceryl Stearate SE | 10.00 |
| | Isopropyl Myristate | 5.00 |
| | Preservative | q.s. |
| | Dimethicone | 1.00 |
| B | Glycerin | 5.00 |
| | Compound of formula (I) or formula (II) according to the present invention such as in particular gambogic amide | 0.05 |
| | Disodium EDTA | 0.20 |
| | PVP | 2.00 |
| | Aqua | Ad 100 |
| C | Parfum | q.s. |

Heat parts A and B separately to 70° C. Add part A to B and homogenize. Add part C under stirring.

Example 13

Hair Gel

| INCI NOMENCLATURE | wt.-% |
|---|---|
| Carbomer | 0.50 |
| Aqua | Ad 100 |
| Triethanolamine | 0.70 |
| Compound of formula (I) or formula (II) according to the present invention such as in particular gambogic amide | 0.01 |
| PVP | 5.00 |
| Parfum | q.s. |
| PEG-40 Hydrogenated Castor Oil | q.s. |
| Phenoxyethanol (and) Methylparaben (and) Butylparaben (and) Ethylparaben (and) Propylparaben | 0.10 |
| Tocopheryl Acetate | 0.10 |

Combine all ingredients of part 1 and mix intensively until a homogeneous gel is obtained.

Example 14

Hair Gel

| INCI NOMENCLATURE | wt.-% |
|---|---|
| Compound of formula (I) or formula (II) according to the present invention such as in particular gambogic amide | 0.1 |
| Polyquaternium-46 | 2.50 |
| Alcohol denat. | 15.00 |
| Aqua | Ad 100 |
| Parfum | 0.10 |
| Glycerin | 0.10 |
| Hydroxyethylcellulose | 2.00 |

Combine all ingredients of part 1 and mix intensively until a homogeneous gel is obtained.

Example 15

Hair Gel

| INCI NOMENCLATURE | wt.-% |
|---|---|
| Compound of formula (I) or formula (II) according to the present invention such as in particular gambogic amide | 0.005 |
| Corn Starch Modified | 2.00 |
| Chitosan | 0.50 |
| Parfum | q.s. |
| PEG-40 Hydrogenated Castor Oil | q.s. |
| PEG-14 Dimethicone | 0.10 |
| Phenoxyethanol (and) Methylparaben (and) Butylparaben (and) Ethylparaben (and) Propylparaben | 0.10 |
| Aqua | Ad 100 |

Combine all ingredients of part 1 and mix intensively until a homogeneous gel is obtained.

Example 16

Shower Oil

| | INCI NOMENCLATURE | wt.-% |
|---|---|---|
| 1 | MIPA-Laureth Sulfate (and) Laureth-4 (and) Cocamide DEA | Ad 100 |
| | Olive Oil PEG-7 Esters | 5.00 |
| | Persea Gratissima (Avocado) Oil | 35.65 |
| | Compound of formula (I) or formula (II) according to the present invention such as in particular gambogic amide | 0.1 |
| | Tocopherol | 0.10 |
| | Alcohol denat. | 5.00 |
| | Bisabolol | 0.25 |
| | Panthenol | 2.00 |

Combine all ingredients of part 1 and mix intensively until a homogeneous solution is obtained.

Example 17

Semi-Permanent Hair Tinting Formulation

| | INCI Nomenclature | wt.-% |
|---|---|---|
| 1 | Cetearyl Alcohol | 12.00 |
| | Ceteareth-25 | 5.00 |
| | Glyceryl Stearate SE | 2.50 |
| | Oleth-10 | 2.00 |
| | Cetearyl Ethylhexanoate | 0.75 |
| | Glycol Distearate | 0.50 |
| | Polysorbate 60 | 0.50 |
| 2 | Aqua | Ad 100 |
| | Monoethanolamine | 1.00 |
| | Basic Red 51 | 0.15 |
| | Disodium EDTA | 0.05 |
| | Compound of formula (I) or formula (II) according to the present invention such as in particular gambogic amide | 0.05 |
| 3 | Perfume | 0.50 |
| | Hydrolyzed Wheat Protein | 1.00 |

Heat part 1 and 2 to 70° C. Add part 2 to part 1 under stirring. Then incorporate part 3.

Example 18

Permanent Hair Tinting Formulation

| | INCI Nomenclature | wt.-% |
|---|---|---|
| | Part I | |
| A | Cetearyl Alcohol | 9.00 |
| | Sodium Ceteaeyl Sulfate | 3.00 |
| | Glyceryl Stearate | 2.50 |
| | Laureth-2 | 2.00 |
| | Stearamide MEA-Stearate | 0.75 |
| | PEG-5 Cocamide | 0.50 |
| | Oleic Acid | 0.50 |
| | Hair Dye | 0.30 |
| B | Aqua | Ad 100 |
| | Ammonium Sulfate | 2.00 |
| | Sodium Sulfite | 0.50 |
| | Disodium EDTA | 0.05 |
| | Compound of formula (I) or formula (II) according to the present invention such as in particular gambogic amide | 0.1 |
| | Ascorbic Acid | 0.50 |
| | Ammonium Hydroxide | 2.50 |
| | Part II | |
| A | Cetearyl Alcohol | 6.00 |
| B | Aqua | Ad 100 |
| | Hydrogen Peroxide | 9.00 |
| | Sodium Lauryl Sulfate | 3.00 |
| | Disodium Phosphate | 0.15 |
| | Phosphoric Acid | pH 2.0 |

Heat phase A and B of Part I separately to 70° C. Add phase A to phase B under stirring. Adjust the pH to 11.2.

Heat phase A and B of Part II separately to 70° C. Add phase A to phase B under stirring. Adjust the pH.

Combine Parts I and II shortly before use.

Example 19

Pharmaceutical Shampoo

| | INCI Nomenclature | wt.-% |
|---|---|---|
| | Part I | |
| A | Aqua | 50.00 |
| | Compound of formula (I) or formula (II) according to the present invention such as in particular gambogic amide | 5.00 |
| | Methylcellulose | 0.30 |
| | Part II | |
| A | Sodium Laureth Sulfate | 44.50 |
| | Ethylparaben | 0.20 |

Dissolve compound of formula (I) or formula (II) according to the present invention (in particular gambogic amide) in water, add Methylcellulose and stir until dissolved; Mix Ethylparaben with Sodium Laureth Sulfate Mix part 1 with part 2

Example 20

Clear Shampoo

| | INCI Nomenclature | wt.-% |
|---|---|---|
| 1 | Sodium Laureth Sulfate | 50.00 |
| | PEG-7 Glyceryl Cocoate | 3.00 |
| | Cocamidopropyl Betaine | 5.00 |
| | Tocopheryl Acetate | 0.10 |
| | *Borago Officinalis* Seed Oil (and) Tocopherol (and) Ascorbyl Palmitate | 0.30 |
| | PEG-40 Hydrogenated Castor Oil | 4.00 |
| | Perfume | 0.30 |
| | BHT | 0.05 |
| 2 | Panthenol | 1.00 |
| | Disodium EDTA | 0.10 |
| | Aqua | Ad 100 |
| | Methylchloroisothiazolinone (and) Methylisothiazolinone | 0.10 |
| | Compound of formula (I) or formula (II) according to the present invention such as in particular gambogic amide | 0.005 |
| 3 | Sodium Chloride | 2.00 |
| | PEG-150 Pentaerythrityl Tetrastearate | 3.00 |

Add all ingredients of part 1) and part 2) and mix intensively until a homogeneous solution is obtained. Then, add the water under slow agitation and wait until the foam has disappeared. Finally, add carefully the thickening agent like Sodium Chloride or Crothix LVR.

Example 21

Hydrating Shampoo

| | INCI Nomenclature | wt.-% |
|---|---|---|
| 1 | Sodium Laureth Sulfate | 45.00 |
| | Ethylhexyl Methoxycinnamate | 0.30 |
| | Methylchloroisothiazolinone (and) Methylisothiazolinone | 0.10 |
| | Panthenol | 1.00 |
| | PEG-7 Glyceryl Cocoate | 2.00 |
| | Cocamidopropyl Betaine | 10.00 |
| | Glycol Distearate (and) Glycerin (and) Laureth-4 (and) Cocamidopropyl Betaine | 2.00 |
| | Disodium EDTA | 0.10 |
| | Parfum | 0.80 |
| | Polyquaternium-10 | 0.10 |
| | Decyl Glucoside | 10.00 |
| | Sodium Chloride | 1.50 |
| | Compound of formula (I) or formula (II) according to the present invention such as in particular gambogic amide | 0.005 |
| | PEG-18 Glyceryl Oleate/Cocoate | 1.00 |
| | Aqua | Ad 100 |

Add all ingredients and mix intensively until a homogeneous solution is obtained. Add the water under slow agitation and wait until the foam has disappeared. Than add carefully the thickening agent like sodium chloride or Crothix LVR.

The invention claimed is:

1. Method for enhancing and/or to restoring hair growth, said method comprising the step of applying to skin having hair of a human in need of enhancing or restoring hair growth a topical composition comprising an effective amount of a compound of formula (I) or formula (II):

Formula (I)

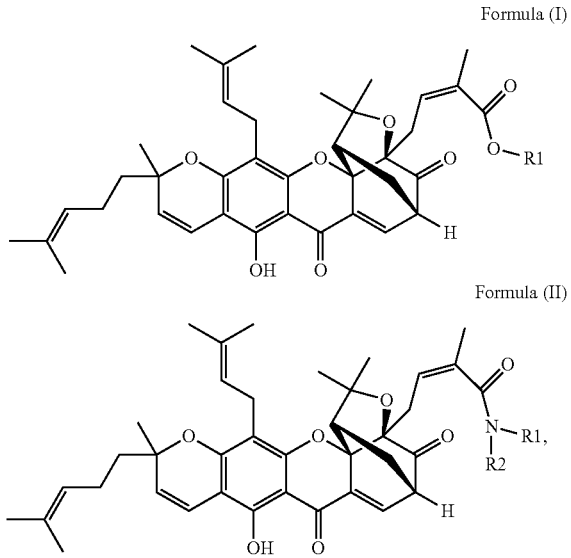

Formula (II)

wherein R1 and R2 are both independently hydrogen (H), or a saturated, straight or branched $C_1$-$C_8$ alkyl group.

2. The method as in claim 1, wherein the compound of formula (I) or formula (II) comprises a gambogic amide of formula (III):

Formula (III)

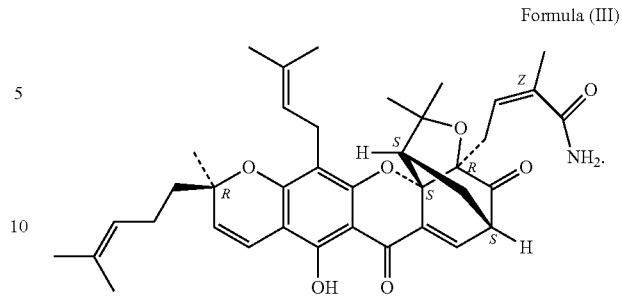

3. The method as in claim 1, wherein the effective amount of the compound of formula (I) or formula (II) is selected in the range of 0.00001 wt.-% to 20 wt.-% based on the total weight of the topical composition.

4. The method as in claim 1, wherein the effective amount of the compound of formula (I) or formula (II) is selected in the range of 0.0001 wt.-% to 1 wt.-% based on the total weight of the topical composition.

5. The method as in claim 1, wherein the topical composition is a hair care composition selected from a hair tonic, a treatment, a conditioner, or a styling gel.

* * * * *